United States Patent [19]

Giuliani et al.

[11] Patent Number: 5,321,019

[45] Date of Patent: Jun. 14, 1994

[54] BILE ACID SULFURATED DERIVATIVES

[75] Inventors: Giangermano Giuliani; Giuliano Frigerio; Roberto Pellicciari, all of Milan, Italy

[73] Assignee: Giuliani S.p.A., Milan, Italy

[21] Appl. No.: 2,971

[22] Filed: Jan. 11, 1993

[30] Foreign Application Priority Data

Jan. 17, 1992 [IT] Italy .................... MI 92A 000082

[51] Int. Cl.⁵ .................... C07J 31/00; A61K 31/575
[52] U.S. Cl. .................... 514/169; 514/182; 552/523; 552/524
[58] Field of Search ............ 552/523, 524; 514/169, 514/182

[56] References Cited

U.S. PATENT DOCUMENTS

| | | | |
|---|---|---|---|
| 5,122,520 | 6/1992 | Azria | 514/182 |
| 5,250,524 | 10/1993 | Kramer et al. | 514/182 |
| 5,266,566 | 11/1993 | Marples et al. | 514/182 |

*Primary Examiner*—Howard T. Mars
*Assistant Examiner*—Kimberly J. Kestler
*Attorney, Agent, or Firm*—Walter H. Schneider

[57] ABSTRACT

Compounds of formula I:

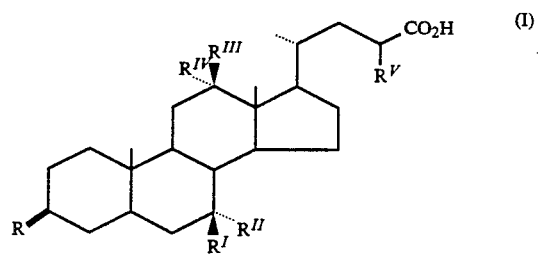

in which the various R groups have the meanings defined in the disclosure are useful as medicaments for the treatment of hepatobiliary diseases.

4 Claims, No Drawings

BILE ACID SULFURATED DERIVATIVES

The present invention relates to bile acid derivatives, a process for the preparation thereof and pharmaceutical compositions containing them.

The derivatives of the invention have the following general formula I:

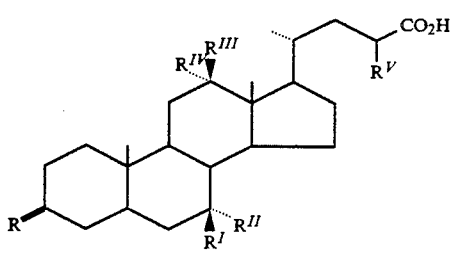

wherein:
R is OH or SH in α- or β- position;
$R^I$ and $R^{II}$ are hydrogen, or one is hydrogen and the other is OH or SH;
$R^{III}$ and $R^{IV}$ are hydrogen or one is hydrogen and the other is OH or SH;
$R^V$ is hydrogen or methyl;
with the proviso that at least one of R, $R^I$, $R^{II}$, $R^{III}$ and $R^{IV}$ is a SH group,
the glyco- or tauro-conjugated derivatives thereof and the pharmaceutically acceptable salts thereof.

Compounds I can be considered as the thio-derivatives of the natural bile acids ursodeoxycholic (UDCA) (3α, 7β OH), ursocholic (3α, 7β, 12α OH), chenodeoxycholic (3α, 7α OH), lithocholic (3α OH), deoxycholic (3α, 12α OH) and cholic (3α, 7α, 12α OH) and of the corresponding 23-methyl derivatives described in EP 135782.

Particularly preferred are the compounds I in which only one of the R, $R^I$, $R^{II}$, $R^{III}$ and $R^{IV}$ groups is SH.

A further preferred group includes compounds wherein either R or $R_I$ is SH and the other groups are different from SH.

The compounds of formula I are useful in therapy as anticholestatic, choleretic, antidyslipemic, hepatocyte-protecting agents as well as for the up to now known traditional uses of the bile acids (treatment of cholelithiasis, bile desaturation, cholesterol metabolic, etc.). Compared with the natural bile acids and the up to now known derivatives thereof, the compounds of the invention show an increased metabolic stability as well as antioxidant and radical scavenging activities, the latter being particularly desirable for the treatment of hepatobiliary pathologies in view of the cyto-protecting effect from exogenous or physiological events (cell aging, toxic metabolites).

The compounds of the invention, for the envisaged therapeutical uses, are administered in form of pharmaceutical compositions prepared according to conventional techniques and excipients, as described for example in "Remington's Pharmaceutical Sciences Handbook", Mack Pub., N.Y. USA.

The preferred administration route is the oral one, whereas the doses, which will vary depending on the pathology to treat and the patient's conditions, in principle will range from 0.5 to 5 g, one or more times daily.

Examples of suitable pharmaceutical forms comprise capsules, tablets, sugar-coated pills, syrups, granulates, solutions, vials. The compounds of the invention can also be used for local perfusion before or after of surgery, in form of solutions or dispersible powders.

The compounds of formula I can be prepared starting from the natural bile acids or the derivatives described in EP 135782, by selective substitution of a OH group with a SH group, according to conventional procedures. For example, the OH group to be replaced will be transformed into a good leaving group, such as a mesyl or tosyl group and then reacted with a sulhydrylation agent such as thiourea, KSH or equivalent reagents, whereas the remaining OH groups will be protected by means of inert groups, under the used reaction conditions.

The substitution reaction can occur with inversion or retention of the α or β stereochemical configuration.

The known difference in chemical reactivity of the OH groups at the 3, 7 and 12 -positions of the bile acids allows to prepare the desired derivatives of formula I by means of suitable schemes of protection/deprotection known to those skilled in the art.

The following example further illustrates the invention.

EXAMPLE a) methyl 3α-7β-diacetoxy-12α-hydroxy-5β-cholanoate

A solution of methyl 3α,7β,12α-triidroxy-5β-cholanoate (10 g, 23.66 mmoles) in benzene (50 ml), pyridine (12.5 ml) and acetic anhydride (12.5 ml) was kept under magnetic stirring in the dark and at room temperature, for 24 hours. The reaction mixture was washed with water (4×40 ml), then with 10% hydrochloric acid to acid pH, then again with water (2×40 ml). The organic phase was evaporated and the residue (10.5 g) was subjected to flash chromatography (SiO₂, h=18 cm, φ=1.7 cm). Eluting first with petroleum ether/ethyl ether 97/3 v/v, then with petroleum ether/ethyl ether 94/6 v/v, the acetylated product is obtained (9.30 g, 77% yield).

NMR (CDCl₃): δ=0.71 (3H, s, C-18 Me); 0.96 (3H, s, C-19 Me); 1.98 (3H, s, C-3 OCOCH₃); 2.01 (3H, s, C-7 OCOCH₃); 3.66 (3H, s, COOMe); 3.90–4.06 (1H, m, C-12 CHOH); 4.43-4.96 (2H, m, C-3 and C-7 CHOAc).

b) methyl 3α,7β-diacetoxy-12αmesyloxy-5β-cholanoate

A solution of methyl 3α-7β-diacetoxy-12α-hydroxy-5β-cholanoate (1.54 g, 2.96 mmoles) in anhydrous pyridine (4,40 ml), kept under magnetic stirring in nitrogen atmosphere at room temperature, was added with methanesulfonyl chloride (0.32 ml, 4.11 mmoles). After 24 hours the reaction mixture was poured into ice-water (50 ml) and extracted with ether (3×40 ml). The combined ether phases were dried over magnesium sulfate, evaporated and washed repeatedly with hexane to remove pyridine. 1.75 g of the mesyl derivative are obtained (quantitative yield) (m.p. 88°–94° C.).

IR (CHCl₃): ν=2950, 2870, (CH₂, CH₃), 1725 (CO), 1335 (SO₂), 905 (SO) cm⁻¹.

NMR (CDCl₃): δ=0.81 (3H, s, C-18 Me); 0.96 (3H, s, C-19 Me); 1.98 (3H, s, C-3 OCOCH₃); 2.01 (3H, s, C-7 OCOCH₃); 3.08 (3H, s, SO₂ Me); 3.65 (3H, s, COOMe); 4.41–4.93 (2H, m, C-3 and C-7 CHOAc); 4.98-5.15 (1H, m, C-12 CHO Ms).

c) 3α,7α-dihydroxy-12β-mercapto-5β-cholan-24-oic acid

A mixture of 3α,7α-diacetoxy-12α-mesyloxy-5β-cholan-24-oic acid (1.90 g, 3.50 mmoles) and thiourea (1.14 g, 3.50 mmoles) in 250 ml of isopropanol was refluxed for 3 hours. Then the reaction mixture was added with a sodium hydroxide solution (30 g) in 300 ml of water and the mixture was refluxed for 2 hours, then it was acidified with diluted sulfuric acid and extracted with several ethyl acetate portions. The combined organic extracts were washed with water and dried over anhydrous sodium sulfate. Then the solvent was evaporated off to obtain a product (65% yield) which, on the basis of the analytical and spectroscopic data, is identified as the 3α,7α-dihydroxy-12β-mercapto-5β-cholan-24-oic acid.

In a similar way, the following compounds I have also been prepared:

3β-mercapto-5β-lithocholan-24-oic acid (Formula I, $R = 3\beta SH$, $R^I = R^{II} = R^{III} = R^{IV} = R^V = H$), obtained from methyl, 3α-hydroxy-5β-litho-24-cholanoate through the following steps:

tosylation of the 3-OH group;
substitution of the 3α-tosyloxy group with potassium thioacetate in DMF and hydrolysis.

M.P. 140°–145° C.

$^1$H-NMR (CDCl$_3$+CD$_3$OD): δ0.7 (s, 3H, 18-CH$_3$), 0.8–1.0 (m, 6H, 19-CH$_3$, 21CH$_3$); 3.55 (m, 1H, 3-C$\underline{H}$).

$^{13}$C-NMR (CDCl$_3$+CD$_3$OD): δ37.1 (3-$\underline{C}$H); 176 (24-$\underline{C}$OOH).

MS-GC: 406 [M-73(Me$_3$Si-)]

3α-mercapto-7α-hydroxy-5β-chenodesoxycholan-24-oic acid (Formula I $R = 3\alpha$ SH, $R^I = R^{III} = R^{IV} = R^V = H$, $R^{II} = OH$), obtained from methyl 3α,7α-dihydroxy-5β-chenodesoxy-24-cholanoate through the following steps:

acetylation of the OH groups;
selective hydrolysis of the 3α acetoxy group in a 9% NaOH methanol solution at room temperature for 30 minutes;
mesylation of the 3α OH group;
substitution of the 3α mesyl group with 3β OH group with concomitant hydrolysis of the 7α acetoxy group;
acetylation of the 3β, 7α hydroxy groups;
selective hydrolysis of the 3β-hydroxy group in a 9% NaOH methanol solution at room temperature for 4 hours;
tosylation of the 3β OH group;
substitution of the 3β-tosyl group with potassium thioacetate in DMF and hydrolysis.

$^1$H-NMR (CDCl$_3$+CD$_3$OD): δ 0.7 (1, 3H, 18-CH$_3$); 0.8–1.0 (m, 6H, 19-CH$_3$, 21-CH$_3$); (m, 1H, 3-C$\underline{H}$); 3.9 (m, 1H, 7-C$\underline{H}$).

$^{13}$C-NMR (CDCl$_3$+CD$_3$OD): δ (3-$\underline{C}$H—SH); 67.6 (7-$\underline{C}$H—OH); 177.0 (24-$\underline{C}$OOH).

3β-mercapto-7α-hydroxy-5β-chenodesoxycholan-24-oic acid, obtained from methyl 3α, 7α-dihydroxy-5β-chenodesoxy-24-cholanoate through the following steps:

acetylation of the OH groups;
selective hydrolysis of the 3α acetoxy group as disclosed above;
tosylation of the 3α OH group;
substitution of the 360 tosyloxy group with potassium thioacetate and hydrolysis.

$^1$H-NMR (CDCl$_3$+CD$_3$OD): δ 0.7 (1, 3H, 18-CH$_3$); 0.8–1.0(m, 6H, 19-CH$_3$21-CH$_3$); 2.5 (m, 1H, 3-C$\underline{H}$); 3.9 (m, 1H, 7-C$\underline{H}$).

MS-GC: 461.50 (M—S—Si—CH$_3$).

We claim:

1. Compounds of formula I:

wherein:
R is OH or SH in α- or β-position;
$R^I$ and $R^{II}$ are hydrogen, or one is hydrogen and the other is OH or SH;
$R^{III}$ and $R^{IV}$ are hydrogen or one is hydrogen and the other is OH or SH;
$R^V$ is hydrogen or methyl;
with the proviso that at least one of R, $R^I$, $R^{II}$, $R^{III}$ and $R^{IV}$ is a SH group,
the glyco- or tauro-conjugated derivatives thereof or the pharmaceutically acceptable salts thereof.

2. Compounds according to claim 1, in which only one of the R, $R^I$, $R^{II}$, $R^{III}$ and $R^{IV}$ groups is SH.

3. A compound according to claim 1, selected from the group consisting of
3α,7α-dihydroxy-12β-mercapto-5β-cholan-24-oic acid,
3β-mercapto-5β-lithocholan-24-oic acid,
3α-mercapto-7α-hydroxy-5β-chenodesoxycholan-24-oic acid, and
3β-mercapto-7α-hydroxy-5β-chenodesoxycholan-24-oic acid.

4. A pharmaceutical composition for the treatment of hepatobiliary diseases comprising as the principal active ingredient an effective amount of a compound according to claim 1 in admixture with a pharmaceutically acceptable carrier.

* * * * *